(12) United States Patent
Huh et al.

(10) Patent No.: US 8,445,465 B2
(45) Date of Patent: May 21, 2013

(54) GLYCOL CHITOSAN DERIVATIVE, PREPARATION METHOD THEREOF AND DRUG DELIVERY SYSTEM COMPRISING THE SAME

(75) Inventors: Kang Moo Huh, Daejeon (KR); Zheng Zheng Li, Daejeon (KR)

(73) Assignee: Chungnam National University Collaboration Foundation, Daejeon (KR)

(\*) Notice: Subject to any disclaimer, the term of this patent is extended or adjusted under 35 U.S.C. 154(b) by 90 days.

(21) Appl. No.: 12/974,841

(22) Filed: Dec. 21, 2010

(65) Prior Publication Data

US 2012/0053331 A1     Mar. 1, 2012

(30) Foreign Application Priority Data

Aug. 30, 2010  (KR) ........................ 10-2010-0083967

(51) Int. Cl.
*A01N 43/04*    (2006.01)
*C08B 37/08*    (2006.01)

(52) U.S. Cl.
USPC ............................................ 514/55; 536/20

(58) Field of Classification Search
USPC .......................................................... 536/20
See application file for complete search history.

(56) References Cited

U.S. PATENT DOCUMENTS

| 6,090,928 A  | * | 7/2000  | Donges et al. ................. 536/20 |
| 6,458,938 B1 | * | 10/2002 | Cha et al. ........................ 536/20 |
| 6,716,970 B2 | * | 4/2004  | Hung et al. ..................... 536/20 |
| 7,683,039 B2 |   | 3/2010  | Hung et al. |

OTHER PUBLICATIONS

Carreno-Gomze, B. & Duncan, R. "Evaluation of the biological properties of soluble chitosan and chitosan microspheres", International Journal of Pharmaceuticals, vol. 148, 2007, pp. 231-240, Elsevier Science B.V.
Knight, D., Shapka S., & Amsden, B., "Structure, depolymerization, and cytocompatibility evaluation of glycol chitosan", Journal of Biomedical Materials Research Part A, Jun. 8, 2007, pp. 787-798, Wiley InterScience.
Kim, K., Kwon, S., Park, J., Chung, H., Jeong, S., Kwon, I., "Physicochemical Characterizations of Self-Assembled Nanoparticles of Glycol Chitosan-Deoxycholic Acid Conjugates", Biomacromolecule, vol. 6, 2005, pp. 1154-1158, American Chemical Society.
Kwon, S., Park, J., Chung, H., Kwon, I., & Jeong, S., "Physicochemical Characteristics of Self-Assembled Nanoparticles Based on Glycol Chitosan Bearing 5â-Cholanic Acid", Langmuir, vol. 19, 2003, pp. 10188-10193, American Chemical Society.

\* cited by examiner

*Primary Examiner* — Elli Peselev
(74) *Attorney, Agent, or Firm* — Kile Park Reed & Houtteman PLLC

(57) ABSTRACT

The present invention relates to a glycol chitosane derivative, a preparation method thereof and a drug delivery system comprising the same. More specifically, the invention relates to a glycol chitosan derivative, which can form nano-sized self-assembled structures and has both temperature sensitivity and biodegradability so as to be suitable for use as a drug delivery system, as well as a preparation method thereof and a drug delivery system comprising the same.

2 Claims, 8 Drawing Sheets

GLYCOL CHITOSAN DERIVATIVE, PREPARATION METHOD THEREOF AND DRUG DELIVERY SYSTEM COMPRISING THE SAME

BACKGROUND OF THE INVENTION

1. Field of the Invention

The present invention relates to relates to a glycol chitosan derivative, which can form nano-sized self-assembled structures and has both temperature sensitivity and biodegradability so as to be suitable for use as a drug delivery system, as well as a preparation method thereof and a drug delivery system comprising the same.

2. Description of the Prior Art

Chitosan is a cationic polysaccharide derived from a chitin which is extracted from the shells of crustaceans such as crabs or shrimps. Generally, chitosan is obtained by removing about 50% or more of acetyl groups of C2 acetamide from chitin and has an N-acetylation degree of less than 50%. It is composed of β(1,4)-linked N-acetyl-D-glucosamine and D-glucosamine units.

Recently, chitosan has received attention as a functional biopolymer which can be used in diverse applications, such as foods, agricultural products, medicines, drugs and cosmetics, because it has various physical and chemical characteristics and physiological characteristics, such as biocompatibility, low toxicity and mucoadhesive properties.

However, chitosan having the above-described characteristics and advantages is insoluble in water, because adjacent molecules of chitosan are linked by a strong hydrogen bond. For this reason, in order to increase the utility of chitosan in the medical and bioengineering fields, it is required to develop chitosan derivatives which can be dissolved in various physiological conditions.

Glycol chitosan is a water-soluble chitosan derivative that is water-soluble at neutral pH due to a hydrophilic ethylene glycol group introduced therein. Previous studies reported that glycol chitosan is non-cytotoxic and biocompatible and stimulates the growth of chondrocytes at low concentration (Carreno-Gomez. B, Duncan. R, Int. J. Pharm. 1997, 148, 231; [8] D. K. Knight, S. N. Shapka, B. G. Amsden, J. Biomed. Mater. Res. Part A. 2007, 83, 787).

The amine groups present along the backbone of glycol chitosan can be modified to improve the in vivo efficiency of glycol chitosan. Glycol chitosan derivatives have been proposed in which various functional groups or molecules are introduced into the backbone of glycol chitosan in order to improve the characteristics of glycol chitosan or to impart new characteristics to glycol chitosan. Kwon et al. improved the hydrophobicity of glycol chitosan by linking 5β cholanic acid or deoxycholic acid thereto by covalent conjugation (K. Kim, S. Kwon, J. H. Park, H. Chung, S. Y. Jeong, I. C. Kwon, I. S. Kim, Biomacromolecules. 2005, 6, 1154; S. Kwon, J. H. Park, H. Chung, I. C. Kwon, S. Y. Jeong, Langmuir. 2003, 19, 10188). In animal studies, the glycol chitosan derivative exhibited extended blood circulation time and showed high tumor specificity in delivering various anticancer agents, such as doxorubicin, paclitaxel, docetaxel, camptothecin and cisplatin.

Although various studies on glycol chitosan derivatives have been conducted as described above, there has not yet been a report of an N-acetylated derivative of glycol chitosan.

SUMMARY OF THE INVENTION

Accordingly, the present inventors have conducted many studies on glycol chitosan derivatives introduced with various functional groups in order to improve the characteristics of glycol chitosan, and as a result, have found that, when glycol chitosan is N-acetylated, the N-acetylated derivative has increased solubility in organic solvent due to the introduction of a hydrophobic acetyl group, shows amphiphilicity to allow for formation of self-assembled structures, and exhibits a sol/gel phase transition behavior, thereby completing the present invention.

It is an object of the present invention to provide a glycol chitosan derivative, which has improved solubility in organic solvent, can form self-assembled structures and can exhibit biodegradability and a sol/gel phase transition behavior, as well as a preparation method thereof.

To achieve the above object, the present invention provides a glycol chitosan derivative having a structure represented by the following formula 1:

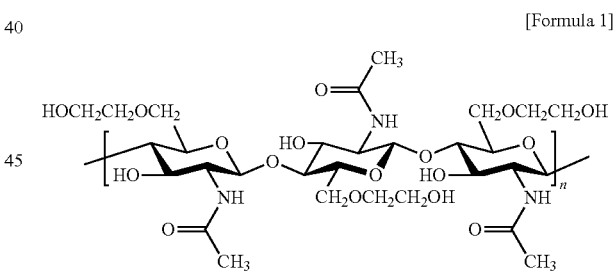

[Formula 1]

wherein n is an integer ranging from 10 to 10000.

The present invention also provides a method for preparing a glycol chitosan derivative of formula 1, the method comprising acetylating a glycol chitosan of formula 2 with an acetylating agent as shown in the following formulas 1 and 2:

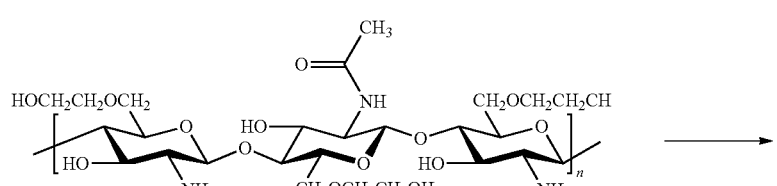

[Formulas 1 and 2]

-continued

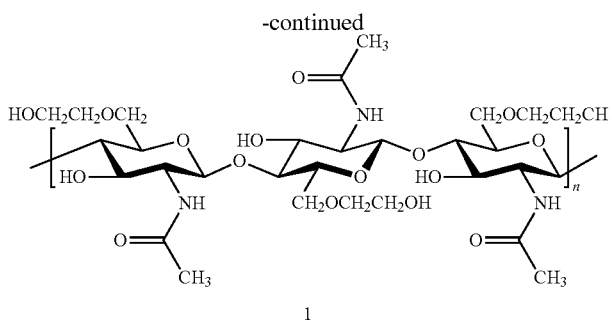

wherein n is an integer ranging from 10 to 10000.

The present invention also provides a drug delivery system comprising said glycol chitosan derivative.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

Hereinafter, the present invention will be described in further detail.

The glycol chitosan derivative according to the present invention is characterized in that the primary amine group of the chitosan backbone is acetylated.

The glycol chitosan derivative introduced with hydrophobic acetyl groups has amphiphilicity. Thus, the glycol chitosan derivative has improved solubility in organic solvents, forms a self-assembled structure in an aqueous medium by a hydrophobic interaction between the acetyl groups, and exhibits a sol-gel behavior according to a change in temperature by intramolecular interactions such as hydrophobic interactions.

Specifically, the glycol chitosan derivative of the present invention is represented by the following formula 1:

[Formula 1]

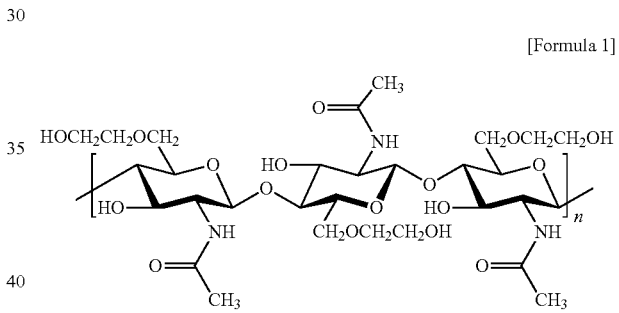

wherein n is an integer ranging from 1 to 10000.

Generally, amphiphilic polymers can form self-assembled nanoparticles in an aqueous atmosphere by a hydrophobic interaction between hydrophobic moieties in order to reduce the surface free energy. Such self-assembled nanostructures have a structure in which a hydrophobic core is surrounded by a hydrophilic shell. The hydrophilic shell can act as a barrier against interactions with other cells, proteins and biological tissues, and the hydrophobic core can act as a space for storing various biochemical substances, and thus can be used for the effective long-term circulation of drugs.

The glycol chitosan derivative according to the present invention has amphiphilicity, because it has a hydrophobic acetyl group introduced into hydrophilic glycol chitosan. Also, a hydrophobic interaction can occur between the main chains of the glycol chitosan derivative. Thus, the glycol chitosan derivative can form self-assembled nanoparticles which are suitable for use in the drug delivery field.

Figure 1:
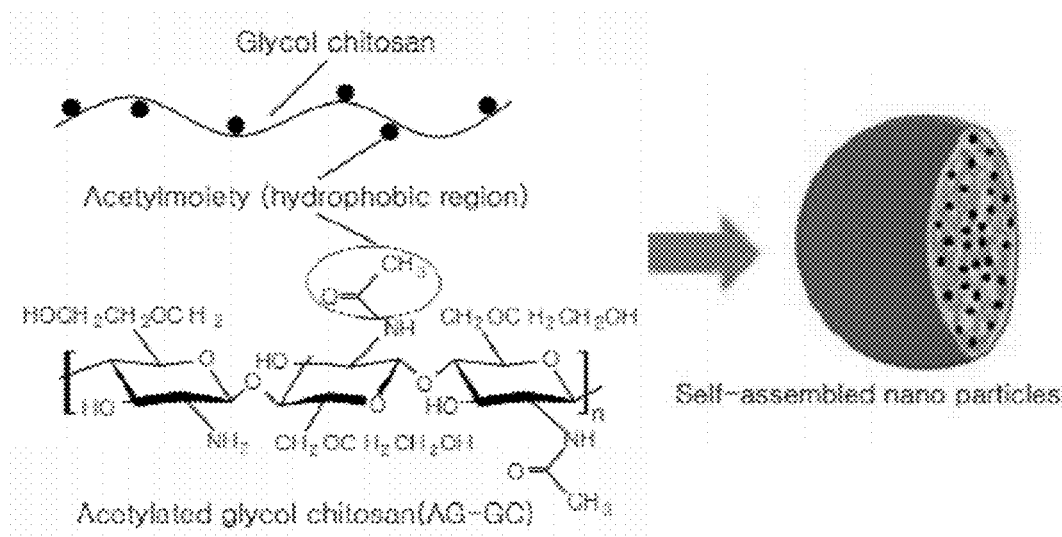
FIG. 1 is a schematic diagram showing the self-assembling property of a chitosan derivative according to the present invention.

FIG. 1 is a schematic diagram showing the self-assembling property of the chitosan derivative according to the present invention.

As shown in FIG. 1, the acetyl group of the chitosan derivative according to the present invention acts as a hydrophobic core, and the glycol chitosan of the derivative acts as a hydrophilic shell. Thus, the chitosan derivative of the present invention can form nanoparticles in an aqueous medium.

The hydrophobic interaction of the acetyl group introduced as described above allows the derivative to form self-assembled structures and to exhibit a sol-gel behavior according to a change in temperature. Thus, the glycol chitosan derivative of the present invention exhibits a phase transition behavior at a temperature of 45±5° C. Because the lower limit of this temperature range is higher than the temperature of the living body, the chitosan derivative of the present invention can be advantageously used for drug delivery.

Also, an acetyl group is a functional group sensitive to digestive enzymes such as lysozyme, and the chitosan derivative of the present invention is biodegradable, because it has the acetyl groups introduced therein.

The above-described characteristics of the glycol chitosan derivative according to the present invention can be controlled depending on the degree of acetylation. For example, as the degree of acetylation increases, the solubility of the glycol chitosan derivative in organic solvent decreases and the biodegradability thereof increases. The acetylation degree of the glycol chitosan derivative is preferably controlled within the range of 20-90%, and more preferably 70-80%.

As shown in the following formulas 1 and 2, the glycol chitosan derivative of the present invention is prepared by acetylating a glycol chitosan of formula 2 with an acetylating agent:

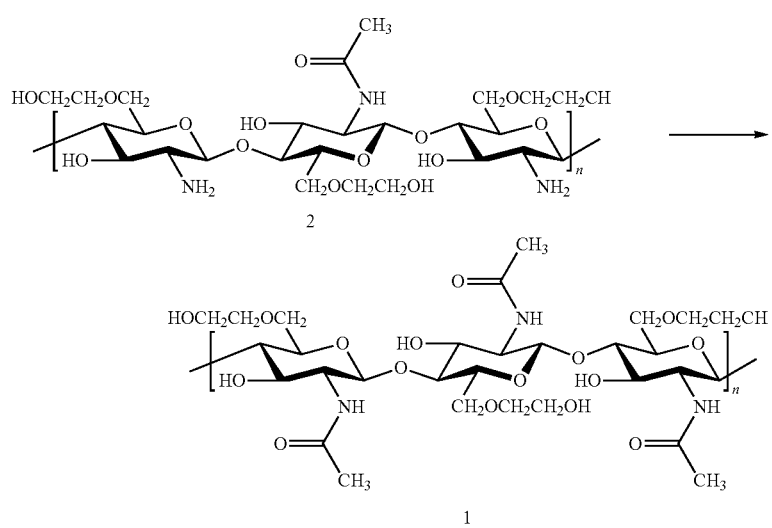

[Formulas 1 and 2]

wherein n is an integer ranging from 10 to 10000.

According to the preparation method of the present invention, the primary amine group of the glycol chitosan of formula 1 is acetylated.

The acetylating agent that is used in the present invention may be selected from among acetic anhydride and acetic chloride. Preferably, acetic anhydride is used.

Although the above-described acetylation may be carried out without using a separate reaction solvent, methanol is preferably used in the acetylation in order to prevent O-acetylation from occurring due to a reaction between the acetylating agent and the hydroxyl group of the main chain. The acetylation reaction is carried out at a temperature between −10 and 60° C., and preferably 15 and 25° C., for 10-50 hours, and preferably 40-50 hours.

The inventive glycol chitosan derivative prepared as described above can form nano-sized self-assembled structures and exhibit a sol-gel behavior according a change in temperature, and thus it can be used as a drug delivery system.

Accordingly, the present invention provides a drug delivery system comprising the glycol chitosan derivative of formula 1. The drug delivery system essentially comprises a pharmaceutically active ingredient. Preferably, the pharmaceutically active ingredient may be a chemotherapeutic agent, a protein drug or a nucleic acid drug.

EXAMPLES

Hereinafter, the present invention will be described in further detail with reference to examples. It is to be understood, however, that these examples are for illustrative purposes only and are not to be construed to limit the scope of the present invention.

Examples 1 to 6

Synthesis of Glycol Chitosan Derivative

According to the following reaction scheme, a glycol chitosan derivative of the present invention was prepared from glycol chitosan.

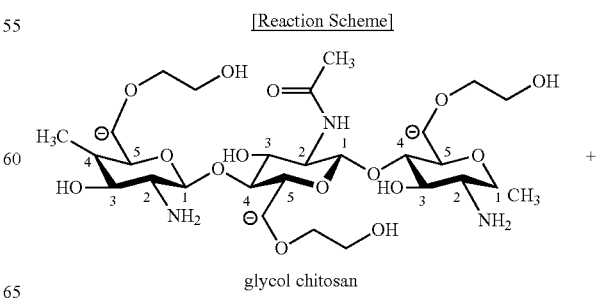

[Reaction Scheme]

glycol chitosan

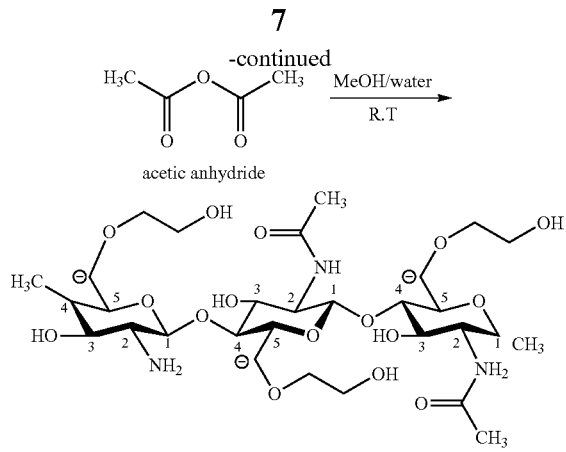

0.2 g of glycol chitosan (weight-average molecular weight: 400 kDa; acetylation degree: 9.34±2.50% (as measured by $^1$H NMR); Sigma-Aldrich, Inc., USA) was dissolved in 25 ml of distilled water, and then diluted with 25 ml of methanol. To the resulting solution, a predetermined amount of acetic anhydride (Sigma-Aldrich, Inc., USA) was added under stirring with a magnetic stirrer. After continuous stirring at room temperature for 48 hours, the stirred solution was precipitated with cold acetone to obtain a reaction product, which was then centrifuged, thereby obtaining a white solid. Then, the resulting reaction product was treated with 1 mol/L of a sodium hydroxide solution for 12 hours to remove the O-acetyl group therefrom. The resulting solution was dialyzed with distilled water for 3 days using a dialysis membrane having a molecular weight cut-off of 2 kDa, and then freeze-dried.

The obtained chitosan derivative was dissolved in $D_2O$ at a concentration of 1 wt % and analyzed by nuclear magnetic resonance ($^1$H NMR, JNM-AL400) at 400 MHz and also analyzed by FT-IR spectroscopy (MAGNA 560) using KBr pellets. The results of the analysis are shown in FIGS. 2 and 3 and Table 1 below.

Figure 2:
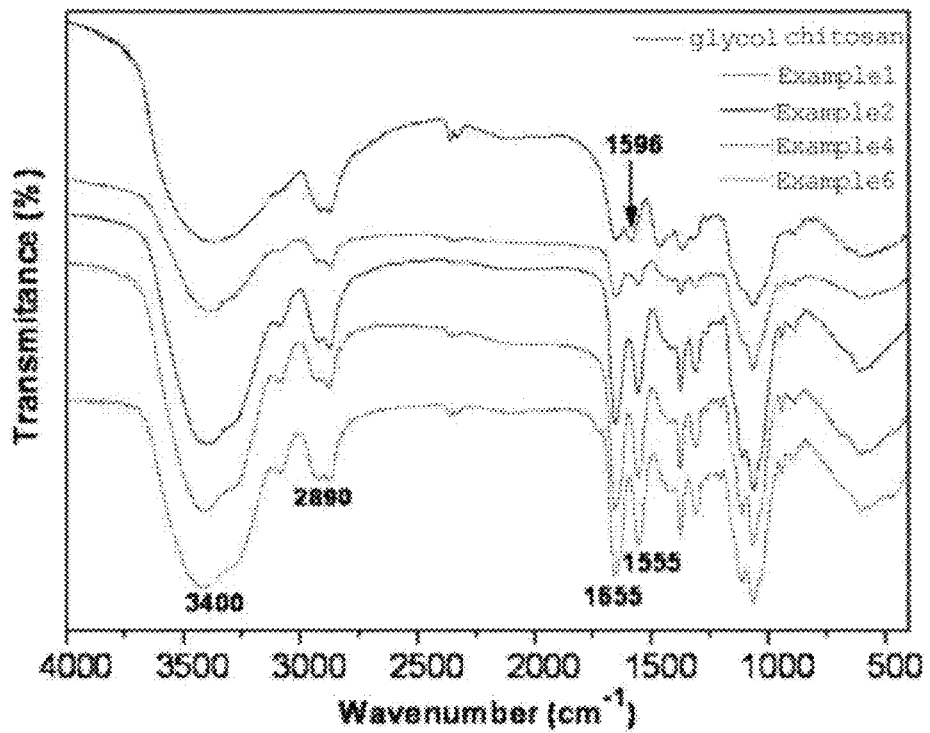
FIG. 2 shows the FT-IR spectra of glycol chitosan and the glycol chitosan derivatives of Examples 1, 2, 4 and 6 according to the present invention.

FIG. 2 shows the FT-IR spectra of glycol chitosan and the glycol chitosan derivatives of Examples 1, 2, 4 and 6 according to the present invention.

Referring to FIG. 2, at 3400 cm$^{-1}$, a broad band caused by OH stretching vibration appeared, and N-H stretching vibration appeared at the same position. At 2890 cm$^{-1}$, an absorption peak caused by the C-H stretching of the methene and methyl groups of glycol chitosan and the glycol chitosan derivatives of the present invention appeared. At 1655 cm$^{-1}$ and 1555 cm$^{-1}$, absorption peaks caused by the stretching of the carbonyl group and the amide II bending vibration appeared. Also, in the case of glycol chitosan, an absorption peak caused by the $NH_2$ bending vibration appeared at 1655 cm$^{-1}$, but in the case of the inventive chitosan derivative in which the amine group was N-acetylated, this characteristic peak was not observed. Meanwhile, the characteristic peak of the ester carbonyl group at 1745 cm$^{-1}$ did not appear, suggesting that the acetylation of glycol chitosan occurred at the amino group, not at the hydroxyl group at the O-position.

Figure 3:
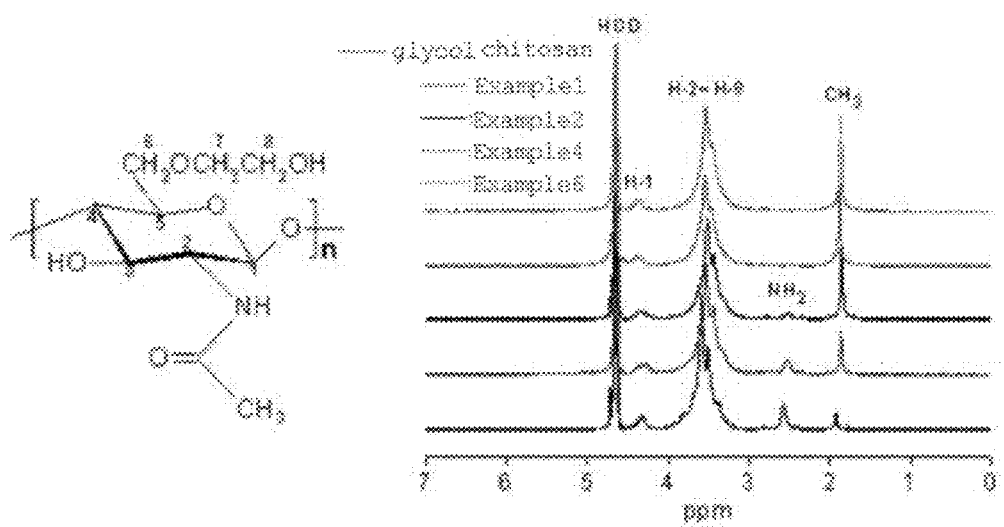
FIG. 3 shows the $^1$H NMR spectra of glycol chitosan and the glycol chitosan derivatives of Examples 1, 2, 4 and 6 according to the present invention.

FIG. 3 shows the $^1$H NMR spectra of glycol chitosan and the glycol chitosan derivatives of Examples 1, 2, 4 and 6 according to the present invention. HOD signal (δ 4.65 ppm) was used as an internal standard.

As shown in FIG. 3, the peak at 1.89 ppm, which generally appears due to the methyl proton of the acetyl group, rapidly increased as the acetylation degree increased. The peak at 2.6 ppm due to the proton of the primary amine group occurred, and it became gradually smaller as the acetylation degree increased. The protons at the positions H-3 to H-8 were all located at the carbon atom close to the oxygen atom. The proton at the 2-position was relatively to the acetyl group and thus showed a downfield shift. Accordingly, overlapping peaks between 3 ppm and 4 ppm occurred by the protons of the glucopyranosyl ring at positions 2, 3, 4, 5, 6, 7 and 8 (from H-2 to H-8). The protons at the H-1 position were bound to two carbon atoms close to the oxygen atom, and thus a peak appeared at 4.38 ppm from downfiled.

In many studies, $^1$H NMR analysis was used to determine the acetylation degree of chitosan, and it may be used to determine the acetylation degree of glycol chitosan. To measure the average degrees of acetylation of glycol chitosan and the glycol chitosan derivatives of the present invention, $^1$H NMR analysis was performed according to the method described in the literature (A. Hirai, H. Odani, A. Nakajima, Polymer Bulletin. 1991, 26, 8). The degree of acetylation was calculated by comparing the integral area of the proton signal (δ 3.55 ppm) at the H-2 to H-8 positions with the integral area of the methyl proton signal (δ 1.89 ppm).

TABLE 1

|  | Molar ratio of acetic anhydride/glucosamine units | Degree of acetylation (%) | Yield (%) |
| --- | --- | --- | --- |
| Glycol chitosan | — | 9.34 ± 2.50 | — |
| Example 1 | 0.2 | 30.78 ± 2.30 | 82.59 |
| Example 2 | 0.5 | 50.58 ± 3.70 | 78.41 |
| Example 3 | 1 | 62.19 ± 1.78 | 70.28 |
| Example 4 | 20 | 75.76 ± 2.60 | 73.24 |
| Example 5 | 60 | 81.30 ± 0.40 | 74.00 |
| Example 6 | 100 | 87.95 ± 3.22 | 77.39 |

As shown in Table 1 above, as the amount of acetic anhydride added to the reaction increased, the acetylation degree of the chitosan derivative also linearly increased. However, in the case of Examples 4 to 6 in which the acetylation degree was high, the effectiveness of the reaction decreased. This is because approach to the amine group becomes more difficult as the N-acetylation progresses.

Experimental Example 1

Examination of Solubility

The solubilities of glycol chitosan and the glycol chitosan derivatives of Examples 1 to 6 in distilled water, DMSO, formamide, DMF, methanol and THF were examined.

Specifically, each of the samples was dissolved in each of the solvents at a concentration of 3 mg/ml, each of the solutions was allowed to stand at room temperature for 24 hours, and the solubility of the solutions was determined based on the turbidity thereof. The results of the experiment are shown in Table 2 below.

TABLE 2

| | Degree of acetylation (%) | Solubility | | | | | |
|---|---|---|---|---|---|---|---|
| | | Distilled water | DMSO | Formamide | DMF | Methanol | THF |
| Glycol chitosan | 9.34 ± 2.50 | + | − | − | − | − | − |
| Example 1 | 30.78 ± 3.70 | + | + | + | − | − | − |
| Example 2 | 50.58 ± 3.70 | + | + | + | ± | − | − |
| Example 4 | 75.76 ± 2.60 | + | ± | − | ± | − | − |
| Example 6 | 87.95 ± 3.22 | + | ± | ± | ± | − | − |

+: soluble;
±: partially soluble or swollen;
−: insoluble

As shown in Table 2 above, the glycol chitosan derivatives of Examples 1, 2, 4 and 6 were all soluble in distilled water without regard to the degree of acetylation, because they contained the hydrophilic ethylene glycol moiety. Also, the glycol chitosan derivatives of Examples 1 and 2 were soluble in DMSO, and it could be seen that the chitosan derivative according to the present invention had improved solubility in organic solvents compared to glycol chitosan. This improvement in solubility makes it possible to enlarge the application of the inventive chitosan derivative in the biomedical and pharmaceutical fields.

Such results are believed to be because the glycol chitosan derivative has the acetyl group introduced therein, and the increase in hydrophobic interactions leads to the decrease in the hydrophilicity of the polymer chain thereof and interferes with the hydrogen bonding between the amino groups of glycol chitosan.

The solubility of the chitisan derivatives of Examples 4 and 6 in organic solvents was not improved. This is because steric hindrance caused by the introduction of a larger number of acetyl groups into the chitosan derivatives. The acetyl groups cause steric hindrance that restricts the rotation of the polymer chain. In other words, as the degree of acetylation increases, the stiffness of the polymer chain increases, whereas the solubility in organic solvent gradually decreases.

Experimental Example 2

Examination of Biodegradability

The biodegradability of the chitosan derivative according to the present invention was evaluated based on the degree of a decrease in viscosity of the polymer solution in the presence of lysozyme. Because lysozyme is present in various human body fluids (plasma, saliva, tear, etc.), it is frequently used to evaluate biodegradation behaviors.

Specifically, an enzymatic degradation experiment was carried out in phosphate buffered saline (PBS, 0.01M, pH 7.4) at 37° C. 40 mg of each of the chitosane derivative samples was dissolved in 20 ml of phosphate buffered saline and then warmed to 37° C. Next, lysozyme was added thereto to a final concentration of 55 µg/ml. A tube containing each of the mixtures was incubated in a constant-temperature water bath (Series BS-21; Lab companion, Korea) at 37° C. and 100 rpm. A change in the viscosity of the mixture was measured with automatic viscosity measuring unit (AVS350; Schott-Cerate). The results of the measurement are shown in FIG. 4.

Figure 4:
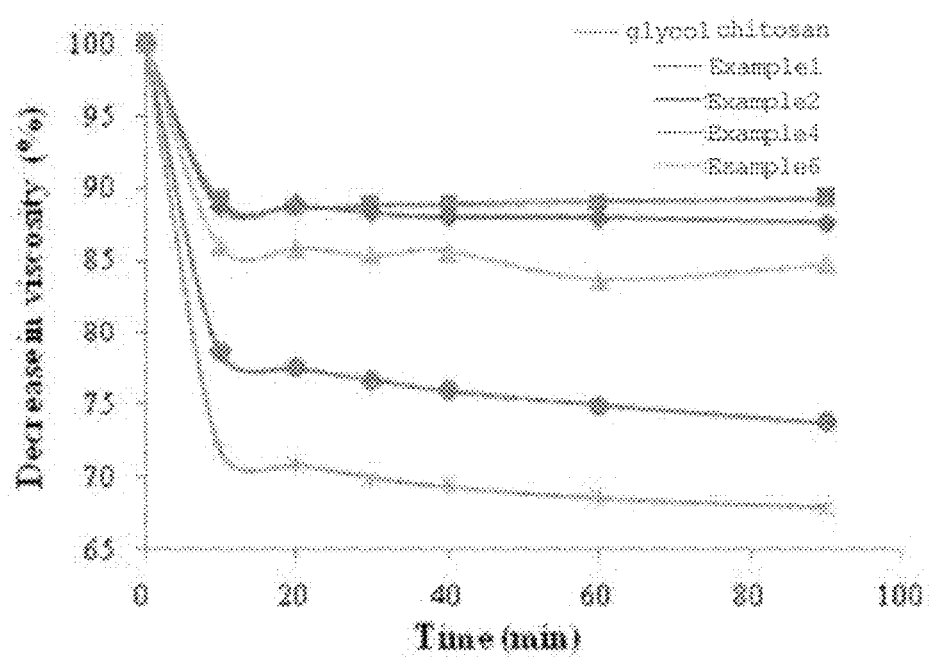
FIG. 4 is a graphic diagram showing the results of observing the changes in viscosity of glycol chitosan and the glycol chitosan derivatives of Examples 1, 2, 4 and 6 according to the present invention in the presence of lysozyme.

As shown in FIG. 4, glycol chitosan and the glycol chitosan derivatives of the present invention showed a remarkable decrease in their viscosity within 10 minutes due to enzymatic degradation caused by lysozyme. Glycol chitosan showed a slow decrease in viscosity, whereas the glycol chitosan derivatives of the present invention showed a rapid decrease in viscosity. This is because the content of the N-acetyl glucosamine residue sensitive to lysozyme is higher in the chitosan derivatives of the present invention than in glycol chitosan.

Such results indicate that the biodegradability of the chitosan derivatives becomes higher as the degree of acetylation increases. In summary, because the degree of acetylation plays an important role in the biodegradability of the chitosan derivatives, the desired biodegradability of the chitosan derivatives in the biomedical field can be achieved by controlling the degree of acetylation thereof.

Experimental Example 3

Examination of Self-Assembly Property

The morphology of nanoparticles formed by self assembly of the chitosan derivative was observed with a scanning electron microscope (FESEM; JSM-7000F; JEOL, Japan) at 15 kV. For this purpose, one drop of distilled water containing the self-assembled chitosan derivative was placed on the surface of a wafer and coated by sputtering at 20 mA for 4 minutes, followed by observation.

The size and distribution of nanoparticles formed by self assembly of the chitosan derivative were measured by dynamic light-scattering (DLS; ELS-Z; OTSUKA, Japan) using a He—Ne laser system with a wavelength of 633 nm.

Figure 5:
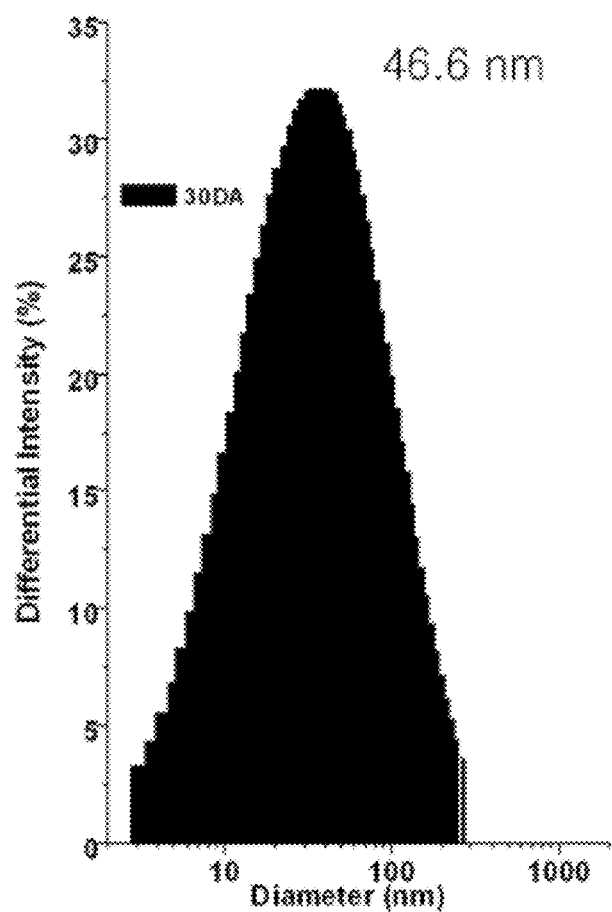
FIG. 5 is a graphic diagram showing the particle size of nanoparticles formed by self-assembly of a glycol chitosan derivative of Example 1.
Figure 6:
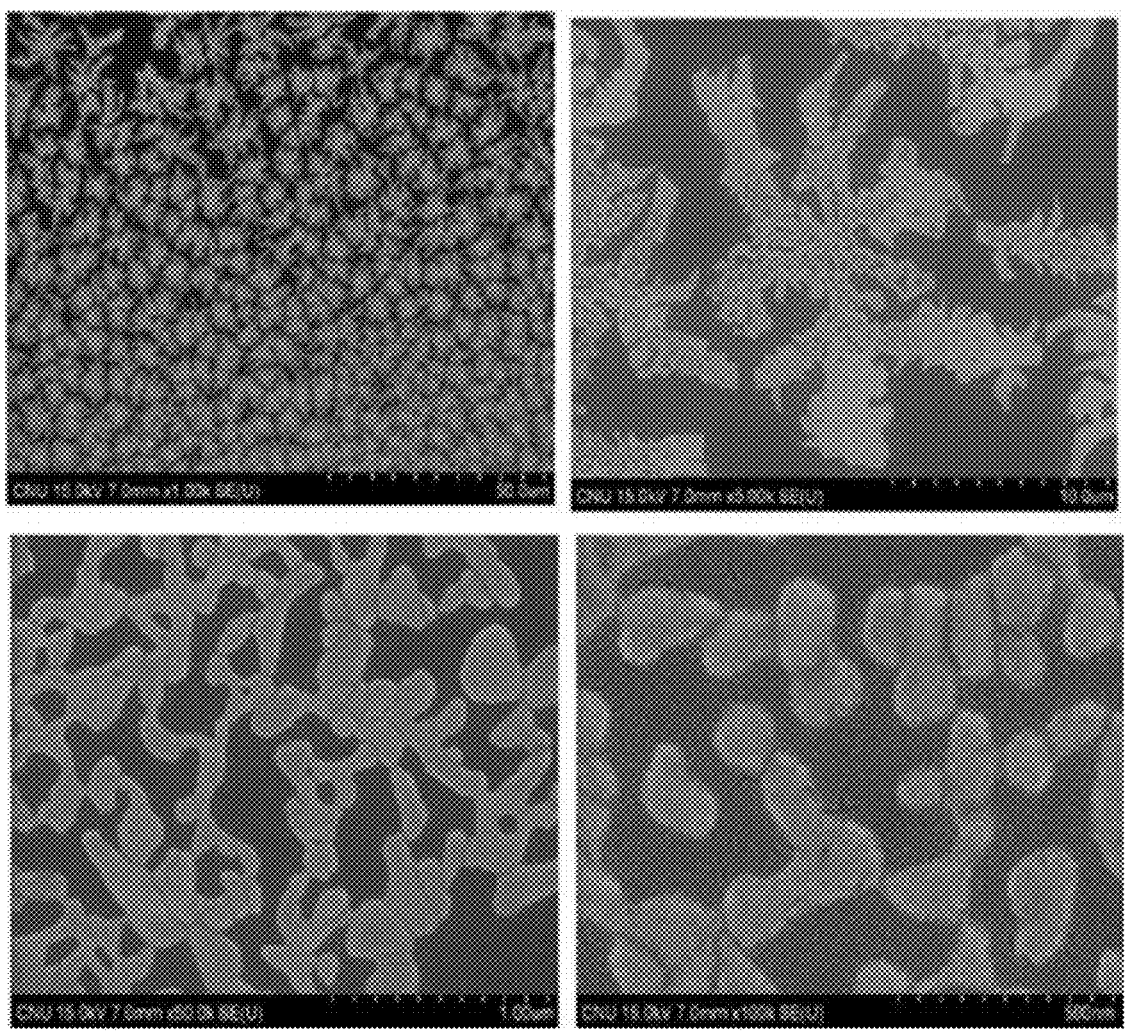
FIG. 6 is a set of scanning electron microscope photographs showing the results of observing nanoparticles formed by self-assembly of a glycol chitosan derivative of Example 1.

FIG. 5 is a graphic diagram showing the particle size of nanoparticles formed by self-assembly of the chitosan derivative of Example 1, and FIG. 6 is a scanning electron microscope photograph showing the results of observing the nanoparticles.

Figure 7:
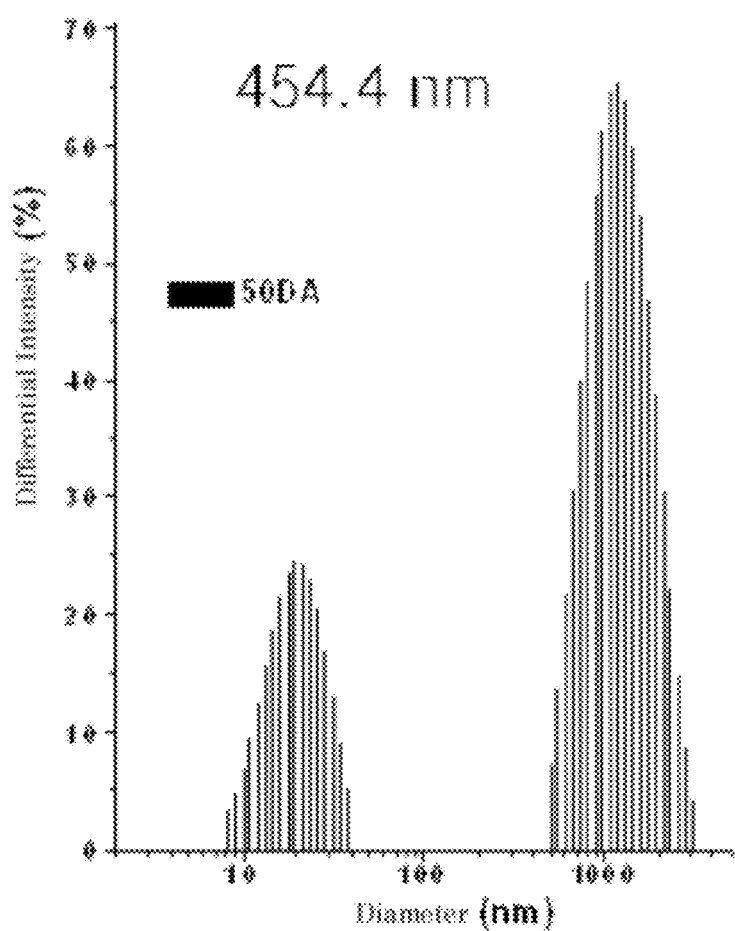
FIG. 7 is a graphic diagram showing the particle size of nanoparticles formed by self-assembly of a glycol chitosan derivative of Example 2.
Figure 8:
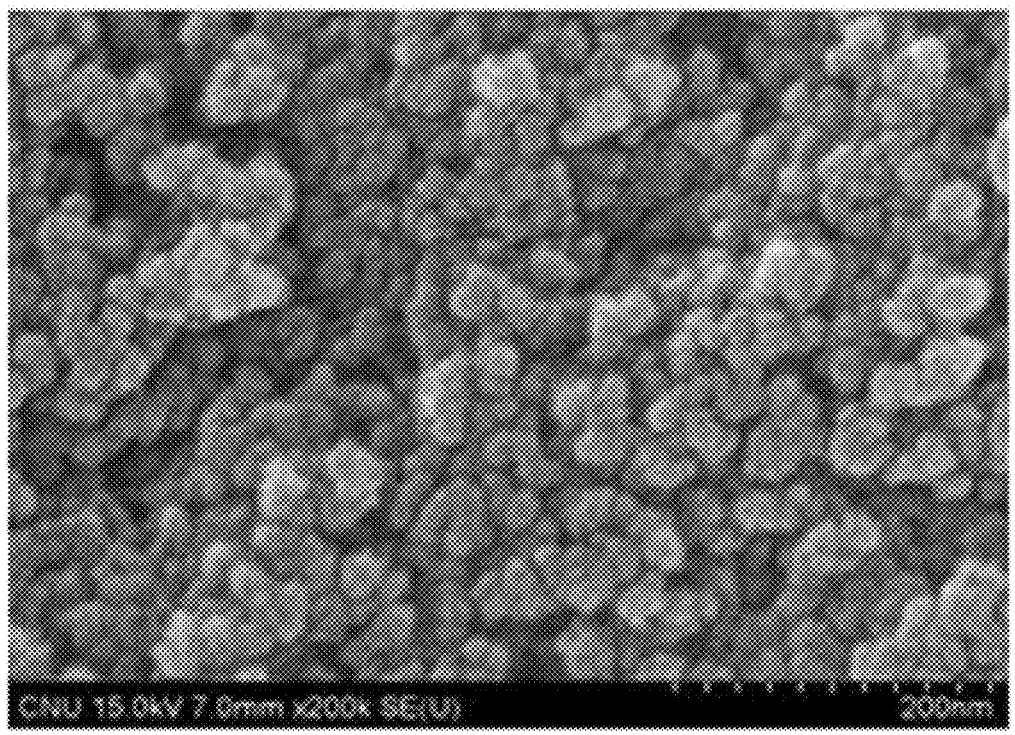
FIG. 8 is a set of scanning electron microscope photographs showing the results of observing nanoparticles formed by self-assembly of a glycol chitosan derivative of Example 2.

FIG. 7 is a graphic diagram showing the particle size of nanoparticles formed by self-assembly of the chitosan derivative of Example 2, and FIG. 8 is a scanning electron microscope photograph showing the results of observing the nanoparticles.

Figure 9:
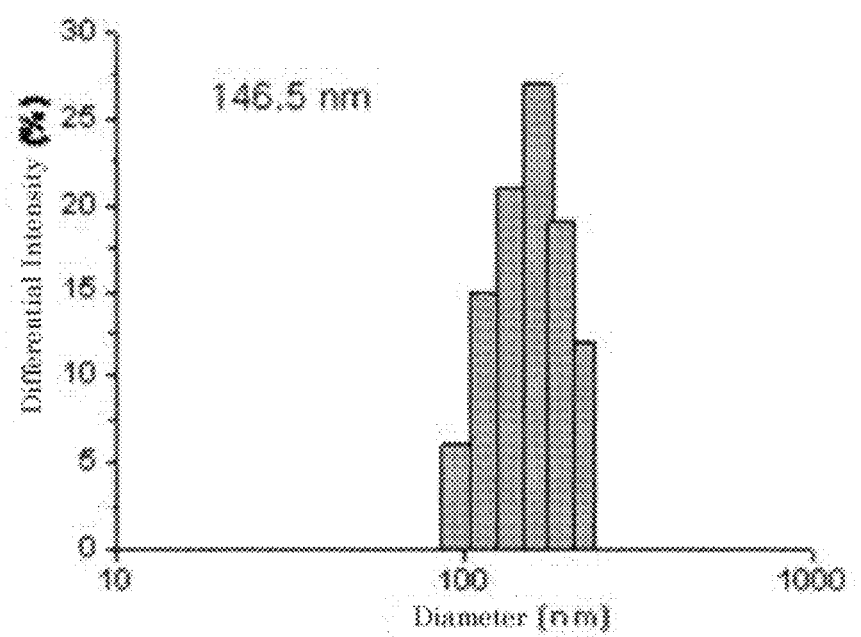
FIG. 9 is a graphic diagram showing the size of nanoparticles formed by self-assembly of a glycol chitosan derivative of Example 4.
Figure 10:
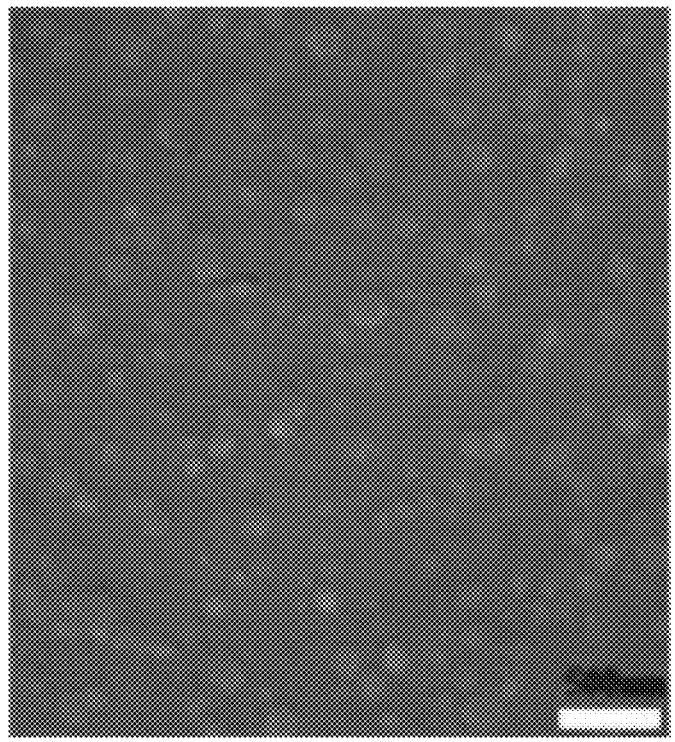
FIG. 10 is a set of scanning electron microscope photographs showing the results of observing nanoparticles formed by self-assembly of a glycol chitosan derivative of Example 4.

FIG. 9 is a graphic diagram showing the particle size of nanoparticles formed by self-assembly of the chitosan derivative of Example 4, and FIG. 10 is a scanning electron microscope photograph showing the results of observing the nanoparticles.

As shown in FIGS. 5 to 10, the nanoparticles formed by self-assembly of the inventive chitosan derivative in an aqueous medium have a spherical particle shape having a size of several tens to several hundreds of nm.

Experimental Example 4

Examination of Temperature-Sensitive Sol-Gel Transition

The sol-gel transition temperature of the chitosan derivative according to the present invention was determined by a test-tube inverting method.

The chitosan derivative was dissolved in distilled water at a concentration of 5 wt % at room temperature to prepare a solution. The sol-gel transition temperature was measured by inverting the test tube at various increasing temperatures and determining the temperature at which the content of the test tube shows a sol state or a gel state. Herein, the rate of increase in temperature was set at 0.2° C./min.

Figure 11:
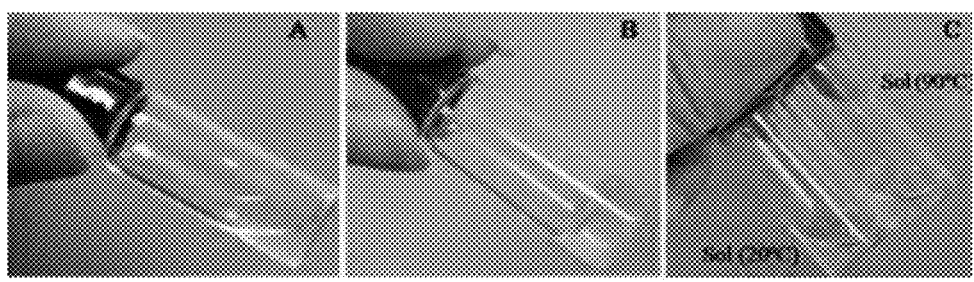
FIG. 11 is a set of photographs showing the sol-gel phase transition behaviors of a glycol chitosan derivative of Example 1 of the present invention and glycol chitosan according to a change in temperature.

FIG. 11 is a set of photographs showing the sol-gel phase transition behavior of the glycol chitosan derivative of the present invention according to the change in temperature.

As shown in FIG. 11, the glycol chitosan derivative of Example 4 showed a sol state at 25° C., but showed a gel state at 45° C.

However, the aqueous solution of glycol chitosan did not show a sol-gel phase transition behavior even when it reached 90° C. Such results indicate that the sol-gel phase transition of the glycol chitosan derivative of the present invention is dependent on the degree of acetylation. This sol-gel phase transition of the glycol chitosan derivative is due to the hydrophobic interaction between the acetyl groups of the polymer. In other words, physical cross-linking occurs due to intramolecular interactions, such as hydrogen bonding and hydrophobic interaction, and the resulting junction zone induces the morphological change (sol-gel behavior) of the chitosan derivative aqueous solution.

As described above, the glycol chitosan derivative according to the present invention has improved solubility in organic solvents, can form nano-sized self-assembled structures and shows a temperature-sensitive sol/gel phase transition behavior. Thus, it is suitable for use as a drug delivery system.

In addition, the glycol chitosan derivative of the present invention can be used in various industrial fields associated with tissue engineering, including materials for drug delivery systems.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A temperature-sensitive N-acetylated glycol chitosan derivative having a structure represented by the following formula 1:

[Formula 1]

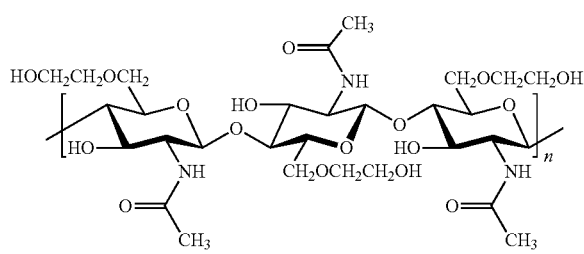

wherein n is an integer ranging from 10 to 10000, and
wherein the glycol chitosan derivative has a degree of acetylation of 70-80%.

2. A drug delivery system comprising the glycol chitosan derivative of claim 1.

* * * * *